United States Patent
Klettke et al.

(10) Patent No.: US 7,923,485 B2
(45) Date of Patent: Apr. 12, 2011

(54) PREPARATIONS BASED ON AZIRIDINO POLYETHERS AND THE USE THEREOF

(75) Inventors: Thomas Klettke, Diessen (DE); Cornelia Führer, Wertach (DE); Adrian Eckert, München (DE); Gunther Eckhardt, Bad Dürrenberg (DE); Erich Wanek, Kaufering (DE)

(73) Assignee: 3M ESPE AG, Seefeld (DE)

( * ) Notice: Subject to any disclaimer, the term of this patent is extended or adjusted under 35 U.S.C. 154(b) by 771 days.

(21) Appl. No.: 10/524,301

(22) PCT Filed: Aug. 4, 2003

(86) PCT No.: PCT/EP03/08615
§ 371 (c)(1),
(2), (4) Date: Oct. 11, 2005

(87) PCT Pub. No.: WO2004/014323
PCT Pub. Date: Feb. 19, 2004

(65) Prior Publication Data
US 2006/0106127 A1    May 18, 2006

(30) Foreign Application Priority Data

Aug. 6, 2002  (DE) .................................. 102 35 990

(51) Int. Cl.
*A61K 6/10*    (2006.01)
*A61C 9/00*    (2006.01)
*C08G 73/06*   (2006.01)
*C08G 73/00*   (2006.01)

(52) U.S. Cl. .......... 523/113; 523/109; 433/214; 106/35; 525/540; 528/422; 528/423; 528/424

(58) Field of Classification Search .................. 523/109, 523/113; 433/214; 106/35; 525/540; 528/422, 528/423, 424
See application file for complete search history.

(56) References Cited

U.S. PATENT DOCUMENTS

| | | | |
|---|---|---|---|
| 3,453,242 | A | 7/1969 | Schmitt et al. |
| 3,634,400 | A | 1/1972 | Schmitt et al. |
| 4,167,618 | A | 9/1979 | Schmitt et al. |
| 4,532,268 | A | 7/1985 | Jochum et al. |
| 4,867,790 | A * | 9/1989 | Jochum et al. ................... 106/35 |
| 5,130,348 | A | 7/1992 | Zahler et al. |
| 5,569,691 | A | 10/1996 | Guggenberger et al. |
| 6,127,449 | A | 10/2000 | Bissinger et al. |
| 6,383,279 | B1 | 5/2002 | Eckhardt et al. |
| 6,403,751 | B1 | 6/2002 | Engelbrecht et al. |
| 6,599,960 | B1 | 7/2003 | Eckhardt et al. |
| 6,612,836 | B1 | 9/2003 | Engelbrecht |
| 6,867,246 | B2 * | 3/2005 | Nowak et al. .................. 523/109 |
| 6,894,144 | B1 | 5/2005 | Zech et al. |
| 6,906,117 | B2 * | 6/2005 | Nowak et al. .................. 523/109 |
| 6,919,386 | B2 | 7/2005 | Wanek et al. |
| 7,276,545 | B2 * | 10/2007 | Eckhardt et al. ............... 523/109 |
| 2002/0077441 | A1 | 6/2002 | Engelbrecht et al. |
| 2003/0109596 | A1 | 6/2003 | Wanek et al. |
| 2003/0153726 | A1 | 8/2003 | Eckhardt et al. |
| 2004/0014907 | A1 | 1/2004 | Nowak et al. |

FOREIGN PATENT DOCUMENTS

| | | |
|---|---|---|
| DE | 914 325 | 7/1954 |
| DE | 17 45 810 | 1/1970 |
| DE | 15 44 837 | 4/1970 |
| DE | 32 45 052 A1 | 6/1984 |
| DE | 37 28 216 A1 | 3/1988 |
| DE | 43 06 997 A1 | 9/1994 |
| DE | 43 21 257 A1 | 8/1996 |
| DE | 197 11 514 A1 | 9/1998 |
| DE | 197 40 234 A1 | 3/1999 |
| DE | 197 53 456 A1 | 6/1999 |
| DE | 197 53 461 A1 | 6/1999 |
| DE | 199 42 459 A1 | 3/2001 |
| DE | 100 01 747 A1 | 7/2001 |
| DE | 100 18 918 A1 | 11/2001 |
| DE | 100 26 852 A1 | 12/2001 |
| EP | 0 421 371 B1 | 8/1994 |
| GB | 1044753 | 10/1966 |
| WO | WO 00/47165 | 8/2000 |
| WO | WO 0117483 A1 * | 3/2001 |
| WO | WO 01/92373 * | 12/2001 |
| WO | WO 01/92374 * | 12/2001 |

OTHER PUBLICATIONS

ASTM D2849-69, "Standard Methods of Testing Urethane Foam Polyol Raw Materials," Annual Book of ASTM Standards, 1987, vol. 08.02, Plastics (II): d-1601-D3099, Title page and pp. 589-608.

ASTM D2849-69, "Standard Methods of Testing Urethane Foam Polyol Raw Materials," Annual Book of ASTM Standards, 1981, Part 36, Plastics—Materials, Film, Reinforced and Cellular Plastics; High Modulus Fibers and Their Composites, Title page and pp. 635-655.

DIN 50125 "ICS 77.040.10 Prüfung metallischer Werkstoffe—Zugproben," (in German) (Also included is an English translation: ICS 77.040.10 Testing of metallic materials—Tensile test pieces), 11 pgs (English translation, 10 pgs) (Jan. 2004).

DIN 53505 "ICS 83.060 Härteprüfung nach Shore A and Shore D," (in German) (Also included is an English translation: ICS 83.060 Testing of Rubber and Elastomers Shore A and Shore D Hardness Test), 5 pgs (English Translation, 8 pgs) (Aug. 2000).

(Continued)

*Primary Examiner* — Mark Eashoo
*Assistant Examiner* — Michael Pepitone
(74) *Attorney, Agent, or Firm* — Loren Albin

(57) ABSTRACT

The invention relates to preparations based on aziridino polymers and comprising monofunctional aziridines and to the use thereof in producing dental materials, especially impression materials.

15 Claims, No Drawings

OTHER PUBLICATIONS

EN ISO 4823:2000, Deutsche Fassung Zhahnheilkunde Elastomere Abformmassen (ISO 4823:2000) 36 pgs, in German [Also included is a translation in English: International Standard, ISO 4823 "Dentistry—Elastomeric impression materials," Third Edition, Dec. 12, 2000, 38 pgs.].

O.C. Dermer, G.E. Ham, Eds.,*Ethylenimine and other Aziridines*, Academic Press, 1969, Title page, Publication page, and Table of Contents (4 pgs. total).

Houben-Weyl, "Methoden der Organischen Chemie," Bd. E5/Teil 1, Georg Thieme Verlag, Stuttgart, 1963, Title page and pp. 658-673. [Also included is a translation in English: Houben-Weyl, *Methods in Organic Chemistry*, "Carbonic acids and carbonic acid derivatives," Expanded and follow-on volumes to the 4$^{th}$ Edition, vol. E-5/part 1, George Thieme Publishing Company, Stuttgart, 1963, 24 pgs.].

Houben-Weyl, "Methoden der Organischen Chemie," 14/2, p. 17, Georg Thieme Verlag, Stuttgart, 1963 [Also included is a translation in English: Houben-Weyl, *Methods in Organic Chemistry*, "Saturated Polyester from two components, " George Thieme Publishing Company, Stuttgart, 1963, 2 pgs].

"Ullmans Encyklopädie der industriellen Chemie," 4. Aufl., Band 11, S. 469 [Also included is a translation in English: *Ullman's Encyclopedia of Technical Chemistry*, "Mineral Oils and Natural Gas to Formazan Colors," 4$^{th}$ newly revised and expanded edition, vol. 11, Chemie Publishing, Weinheim/Bergstrasse, 3 pgs.].

* cited by examiner

PREPARATIONS BASED ON AZIRIDINO POLYETHERS AND THE USE THEREOF

The present application is a U.S. National Stage Application of PCT/EP2003/008615, filed 4 Aug. 2003. The application also claims the benefit under 35 U.S.C. §119 of foreign application no. DE 102 35 990.3, filed 6 Aug. 2002.

The invention relates to preparations based on aziridino polymers and comprising monofunctional aziridines and to the use thereof in producing dental materials, especially impression materials.

Making an impression of the specific features inside the mouth of a patient using suitable impression materials is a prerequisite for the production of exactly fitting dentures, crowns and bridges, inlays and onlays. Amongst the known impression materials, the materials which are based on aziridino polyethers are outstanding, by virtue of their inherently hydrophilic nature and their flow properties in the cured state, as a result of which high-precision impressions are obtained.

However, when making an impression of the specific features inside the mouth of the patient using suitable impression materials, the fact that the impression-taking procedure is unpleasant for the patient often causes problems. For that reason, the time for which a suitable impression material remains in the patient's mouth should be short. However, premature removal of the impression material can result in a loss of accuracy and modelling sharpness with respect to reproduction of the mouth's features if the impression material has not yet cured sufficiently.

For that reason, attempts have, at various times, been made at accelerating the hardening time of the impression materials used, for example by using an increased amount of catalyst or different polymeric binders. Generally, however, the consequence thereof has been that the elastomeric properties of the cured impression material have deteriorated.

In addition, in the case of the impression materials known from the prior art, large amounts of plasticisers often have to be used. However, because the plasticisers are not chemically bonded into the polymeric network of the cured impression, migration of the plasticisers to the surface of the impression may occur when the impressions are stored, as a result of which the subsequent making of casts from the impressions is often adversely affected.

There is accordingly a need for impression materials which allow the dentist sufficient working time before the impression material cures but which cure as fast as possible in the patient's mouth at least to the extent that the time in the mouth can be reduced to a necessary minimum and the treatment can accordingly be made more pleasant for the patient. There has furthermore been a need for impression materials which, despite having a lower plasticiser requirement, have excellent mechanical properties and good long-term stability.

The preparation of polymers carrying aziridino groups and the use thereof in dental materials has been known for a long time. For example, DE 174 58 10 C describes the production of moulded articles based on aziridino polyethers. Even though the possibility is mentioned therein of also using impression materials having a content of monofunctional aziridines, this is described, however, as being disadvantageous in respect of the mechanical properties. An acceleration effect in respect of curing of the dental materials is not described in the mentioned publication.

DE 100 26 852 A1 relates to N-alkyl-aziridino block copolymers which have a polysiloxane framework. The possibility of obtaining an accelerated curing time by adding monofunctional aziridines is not disclosed in the publication.

The problem of the present invention was accordingly to make available dental materials based on aziridino polymers which are distinguished by accelerated curing whilst still having an adequate processing time (open time). A further problem of the invention was, especially, to make available dental materials based on aziridino polymers which, in comparison to the dental materials known from the prior art, reach high values of Shore A hardness more quickly, whilst the completely cured materials have Shore A hardnesses which are located within a desired range and are substantially the same as in the case of the dental materials known from the prior art.

The problem is solved by preparations, and dental materials produced therefrom, as are described in the context of the text hereinbelow.

The present invention accordingly relates to a composition comprising at least the two components Z1 and Z2, the composition comprising,
a) as component Z1, at least one polyaddition product or at least one polycondensation product having on average 2 aziridino groups or more and a molecular weight of at least 1000 and,
b) as component Z2, at least one compound having 1 aziridino group, at least one compound according to component Z2 differing, in its chemical make-up, from at least one compound according to component Z1 in at least one further feature other than the number of the aziridino groups.

In the context of the present text, a "composition" is understood to be a mixture of two or more compounds, as is explained in the context of the present text.

A composition according to the invention comprises at least two components Z1 and Z2, component Z1 representing a polyaddition product or a polycondensation product having on average 2 aziridino groups or more and a molecular weight of preferably at least 1000.

The term "molecular weight" refers herein to the number average of the molecular weight, as is conventionally determined for the individual classes of polymers by gel permeation chromatography (GPC) against a standard of defined molecular weight. Suitable measurement methods will be known to the person skilled in the art.

Furthermore, the determination of the molecular weights and the molecular weight distribution of polymeric polyols can be carried out, for example, by means of end group determination, for example by nuclear magnetic resonance (NMR) methods. Also suitable for the determination of the molecular weights and the molecular weight distribution of polymeric polyols is the determination of the hydroxyl value, as is described, for example, in Houben-Weyl "Methoden der organischen Chemie", 14/2, p. 17, Georg Thieme Verlag, Stuttgart, 1963. Also suitable is the procedure described in ASTM D2849—Method C.

An especially suitable method of determining the molecular weight ($M_w$ and $M_n$) and molecular weight distribution of organic diols can be carried out, for example, by means of GPC using a column combination PSS SDV 10,000 Å+PSS SDV 500 Å+PSS SDV 100 Å with column dimensions of 8×300 mm and a particle size of 5 µm. As a pre-column there is used a PSS SDV 100 Å having column dimensions of 8×50 mm and a particle size of 10 µm. THF stabilised with 200 ppm of Ionol, at a flow rate of 1.0 ml/min, is especially suitable as the mobile phase. As the detector there is used a refractive index (RI) detector; the injection volume for the samples (1% w/w weighed into the mobile phase) is 100 µl. As the standard solution there is used a polystyrene standard series (0.1% w/w weighed into the mobile phase). The evaluation is carried out according to the principle of relative GPC using an automatic evaluation module (TurboSEC Software) by means of comparison of the volumes of sample eluted with the volumes of the polystyrene standard series eluted. $M_n$, $M_w$ and polydispersity are evaluated.

In principle all polymers which can be prepared by polycondensation methods are suitable in the context of the present invention as polycondensation products, provided that they meet the requirements of the composition with respect to their preferred use as dental materials. Suitable polycondensation products are, for example, polyesters, polyacetals or polysiloxanes.

Among the known, variously constituted, polyesters, those that are obtainable by polycondensation of dicarboxylic acids with diols or by polycondensation of oxycarboxylic acids and that have a substantially linear structure are especially suitable for preparation of the starting materials. The concomitant use of small amounts of tri- or tetra-functional alcohols or carboxylic acids during the polycondensation is possible and, in many cases, even advantageous for the mechanical properties of the compositions obtainable from the polyesters with respect to the use thereof as dental materials.

A large number of polyols can be used as polyols for the preparation of the above-mentioned polyesters. They are, for example, aliphatic alcohols having from 2 to 4 OH groups per molecule. The OH groups may be either primary or secondary. Suitable aliphatic alcohols include, for example, ethylene glycol, propylene glycol, 1,4-butanediol, 1,5-pentanediol, 1,6-hexanediol, 1,7-heptanediol, 1,8-octanediol and higher homologues or isomers thereof, as the skilled person will obtain by stepwise extension of the hydrocarbon chain in steps of one $CH_2$ group or by introducing branches into the carbon chain. Also suitable are higher-functional alcohols such as, for example, glycerol, trimethylolpropane, pentaerythritol and also oligomeric ethers of the mentioned substances either alone or from a mixture of two or more of the mentioned ethers together.

The reaction products of low-molecular-weight polyfunctional alcohols with alkylene oxides, so-called polyethers, may also be used as polyols. The alkylene oxides preferably have from 2 to 4 carbon atoms. There are suitable, for example, the reaction products of ethylene glycol, propylene glycol, butanediol or hexanediol isomers with ethylene oxide, propylene oxide or butylene oxide, or mixtures of two or more thereof. Furthermore, the reaction products of polyfunctional alcohols such as glycerol, trimethylolethane or trimethylolpropane, pentaerythritol or sugar alcohols, or mixtures of two or more thereof, with the mentioned alkylene oxides, forming polyether polyols are also suitable.

Appropriate polyethers are brought about in a manner known to the person skilled in the art by reaction of the starting compound having a reactive hydrogen atom with alkylene oxides, for example ethylene oxide, propylene oxide, butylene oxide, styrene oxide, tetrahydrofuran or epichlorohydrin or mixtures of two or more thereof.

Suitable starting compounds are, for example, water, ethylene glycol, 1,2- or 1,3-propylene glycol, 1,4- or 1,3-butylene glycol, 1,6-hexanediol, 1,8-octanediol, neopentyl glycol, 1,4-hydroxymethylcyclohexane, 2-methyl-1,3-propanediol, glycerol, trimethylolpropane, 1,2,6-hexanetriol, 1,2,4-butanetriol, trimethylolethane, pentaerythritol, mannitol, sorbitol, or mixtures of two or more thereof.

For the preparation of appropriate polyesters there are suitable, for example, succinic acid, adipic acid, suberic acid, azelaic acid, sebacic acid, phthalic acid, isophthalic acid, terephthalic acid, trimellitic acid, phthalic anhydride, tetrahydrophthalic anhydride, hexahydrophthalic anhydride, tetrachlorophthalic anhydride, endomethylenetetrahydrophthalic anhydride, glutaric anhydride, maleic acid, maleic anhydride, fumaric acid, dimer fatty acid or trimer fatty acid or mixtures of two or more thereof. Where appropriate, minor amounts of monofunctional fatty acids may be present in the reaction mixture. Likewise suitable are unsaturated dicarboxylic acids such as maleic acid or fumaric acid and aromatic dicarboxylic acids, for example the phthalic acid isomers such as phthalic acid, isophthalic acid or terephthalic acid. As tricarboxylic acids there are suitable, for example, citric acid or trimellitic acid. The mentioned acids may be used singly or in the form of mixtures of two or more thereof.

The polyesters may, where appropriate, have a small proportion of carboxyl end groups. Polyesters obtainable from lactones, for example ε-caprolactone, or hydroxycarboxylic acids, for example ω-hydroxycaproic acid, may also be used.

Polyacetals are also suitable as polyol condensation products. Polyacetals are understood to be compounds such as are obtainable from glycols, for example diethylene glycol or hexanediol or a mixture thereof, with formaldehyde. Polyacetals which can be used in the context of the invention may also be obtained by the polymerisation of cyclic acetals.

As polysiloxanes there are suitable, in principle, all polysiloxanes which meet the requirements in terms of material properties with regard to the preferred use as dental materials. Special preference is given in the context of the present invention, however, to, for example, the polysiloxane basic structures of the aziridino-group-carrying polysiloxanes described in DE 100 26 852 A1 from p. 2, line 55 to p. 8, line 20. The disclosure of the mentioned publication is regarded as part of the disclosure of the present text.

As polyaddition products there are suitable in the context of the present invention, in principle, all polymers which can be prepared by polyaddition methods provided that they meet the requirements of the composition with regard to the preferred use thereof as dental materials. Suitable polyaddition products are, for example, polyurethanes or polyethers.

As polyurethanes there are suitable, in principle, all polymers which can be prepared by the reaction of polyols or polycarboxylic acids and isocyanates. Appropriate preparation methods will be known to the person skilled in the art; suitable polyols have already been described in the context of the present text as starting materials for the preparation of the above-mentioned polyesters.

In the context of a preferred embodiment of the present invention, there are used, as constituents of the compositions according to the invention, polyaddition products, these preferably being polyethers.

As polyethers there are suitable, in principle, all polyether compounds which meet the requirements in terms of material properties with regard to the preferred use as dental materials. Suitable polyethers and processes for their preparation are described, for example, hereinbefore in the context of the present text. Especially suitable are polyether compounds as are obtainable by polyaddition of ethylene oxide, 1,2-propylene oxide, 1,2-butylene oxide or tetrahydrofuran or of mixtures of two or more of the mentioned compounds with the aid of a suitable starting compound and a suitable catalyst.

However, in the context of the present invention, polyether compounds having a constituent of at least one repeating unit derived from 1,2-propylene glycol in the polyether chain are especially suitable. Accordingly, as basic polyether frameworks for the aziridino-group-carrying polymers contained in a composition according to the invention there are suitable, for example, polypropylene glycol or ethylene glycol/propylene glycol copolymers or tetrahydrofuran/propylene glycol copolymers or tetrahydrofuran/ethylene glycol copolymers or mixtures of two or more thereof, especially polypropylene glycol or ethylene glycol/propylene glycol copolymers or tetrahydrofuran/ethylene glycol copolymers.

For example, polyether polyols which are prepared by copolymerisation of tetrahydrofuran and ethylene oxide in a molar ratio of from 10:1 to 1:1, preferably to 3:1, in the presence of strong acids, for example boron fluoride etherates, are suitable.

The polyether polyols which can be used for preparation of component Z1 have, on average, at least 2 hydroxyl groups but may also have up to 20 hydroxyl groups per molecule, for example on average up to about 3, 4, 5, 8, 10 or 15 hydroxyl groups.

The molecular weights ($M_n$) of the polyether polyols are usually in the range from 600 to 20,000 g/mol, preferably in the range from about 1,000 to 10,000 g/mol.

The distribution of the structural units in the polymer which are based on different monomers can be organised randomly or in blocks.

Furthermore, suitable polyethers are described in DE PS 1 745 810, the disclosure of which in that respect is regarded as part of the disclosure of the present text.

The polymers contained, in the context of the present invention, as component Z1 in the compositions according to the invention carry, on average, at least 2 aziridino groups.

The term "on average" is to be so interpreted in the context of the present text that a mixture of a large number of compounds of component Z1 may comprise both compounds having less than 2 aziridino groups and also compounds having more than 2 aziridino groups although, when seen over the entirety of the compounds of component Z1, the average functionality of all molecules is, with respect to aziridino groups, 2 or more.

All mentioned types of polyaddition or polycondensation products can be provided with aziridino groups by means of any desired subsequent reactions known to the person skilled in the art. For example, it is possible first to introduce, into an appropriate polymer, substituents which are in turn capable of reacting with suitable aziridine derivatives. It is often possible to polymerise cyclic ethers, preferably epoxides, onto the chain so that products are obtained which at the end contain substituents which can react with aziridine. There come into consideration, for example, polyethers onto which halo-substituted epoxides, e.g. epibromohydrin, are polymerised. These substances contain short halo-substituted end groups, for example $CH_2Br$ groups when using epibromohydrin.

In the case of polyethers, the OH end groups thereof can also be replaced by halogen atoms, after which the halogen atoms are converted, for example with excess ammonia or potassium phthalimide, into amino groups, which are then caused to react with ethyleneiminocarboxylic esters. Because the halogenated polyethers act as alkylating agents and can therefore trigger unintended cross-linking reactions, it should be ensured that the halogen atoms are replaced as completely as possible, for example by amino groups, or that any residual halogen is removed, for example by treatment with alkali alcoholate.

A further process for the preparation of aziridino-group-carrying polymers consists in the acylation of OH-group-carrying polyaddition or polycondensation products using halocarboxylic acids and subsequent reaction with appropriate aziridine derivatives. In that case, α-halocarboxylic acids, e.g. chloroacetic acid or bromobutyric acid, are especially suitable. The acylation in the context of the two mentioned processes can, of course, be carried out in various ways, for example by means of acid-catalysed esterification or by using acid anhydrides or acid chlorides.

A further route leading to the compounds which can be used in accordance with the invention is the reaction of OH-group-containing polymers with at least bifunctional isocyanates, preferably diisocyanates, for example 2,4-tolylene diisocyanate, 4,4'-diphenylmethane diisocyanate or naphthalene 1,5-diisocyanate. In the case of that reaction, it is often advantageous, in order to avoid subsidiary reactions, to proceed at a relatively low temperature, which can be achieved by means of highly active catalysts such as tertiary amines or metal compounds such as zinc acetylacetonate or organotin compounds. These catalysts do not generally disrupt subsequent further processing of the substances. So-called isocyanate-extended polyesters, in which urethane groups are present in the chain, can also be used.

In the subsequent reaction, the polyesters provided with terminal isocyanate groups are made to react with suitable alkyleneimine derivatives. For that purpose there come into consideration, for example, ethyleneimine derivatives having OH groups or primary or secondary amino groups. There may be mentioned ethyleneiminoamines, e.g. γ-ethyleneiminopropylamine and β-ethyleneiminoethylamine, and also ethyleneimino alcohols, e.g. 3-ethyleneiminopropan-1-ol, and also the ethyleneiminoacyl derivatives of at least divalent amines. The last-mentioned substance class has the particular feature, amongst others, that the precursors and end products produced therefrom have amino groups that are only comparatively weakly basic.

Suitable possible methods for providing the polymers with aziridino groups are mentioned, by way of example, in DE PS 1 745 810 or DE 100 26 852 A1; reference is expressly made to the mentioned publications, and the disclosure thereof with respect to functionalising polymers with aziridino groups is understood to be part of the disclosure of the present text.

Polymers suitable as component Z1 can carry the aziridino groups terminally or laterally, or terminally and laterally, but preferably terminally.

The aziridino polymers which can be used as component Z1 should preferably have a dynamic viscosity η of from 10 to about 500 Pa*s, especially from about 15 to about 300 Pa*s (23° C., measured with a rotary viscometer of the CVO 120 HR type from the company Bohlin Instruments GmbH Pforzheim at 23° C., plate-plate geometry, plate diameter: 20 mm, or plate-cone geometry, shear rate 20 $s^{-1}$).

A preferred viscosity range is from about 20 to about 180 Pa*s at 23° C. The aziridino equivalent for the compounds used as component Z1 in the context of the present invention is from about 250 to about 25,000 g/equivalent, especially from about 400 to about 10,000 g/equivalent.

A component Z1 which can be used in accordance with the invention may comprise, in the context of the present invention, only one type of aziridino polymer. It is, however, likewise possible for a component Z1 which can be used in accordance with the invention to comprise two or more different types of aziridino polymers, for example 3, 4 or 5 different types.

A "type of polymer" is understood, in the context of the present invention, to be a polymer as results from the polyaddition or polycondensation of selected monomers under the selected reaction conditions. A type of polymer can accordingly include polymer molecules of differing chemical constitution and differing molecular weight, depending on the reaction conditions selected. However, two reactions carried out using identical monomer compositions under identical reaction conditions always result, in accordance with the invention, in identical types of polymer. Two reactions which are carried out using identical monomers but under different reaction conditions may result in identical types of polymer but need not do so. The crucial factor therein is whether there are identifiable differences—in terms of chemical constitution, molecular weight and further parameters which can be determined—that are of relevance to the material properties. Two reactions which are carried out using different monomer compositions always result, in accordance with the invention, in different types of polymers.

In the context of a preferred embodiment, a component Z1 which can be used in accordance with the invention comprises one type or two different types of aziridino polymer, especially only one type.

The above-described aziridino polymers can usually be used in the form in which they are obtained in the course of preparation, but they may also be purified in order to obtain especially lightly coloured and high-quality products. For that purpose there come into consideration the customary methods, for example filtration, optionally in solution, over kieselguhr, aluminium oxide, treatment with ion exchangers, washing of the solutions in organic solvents using water, aqueous alcohol, salt solutions and the like, and also optionally repeated reprecipitation, for example from aromatic solvents or alcohols. Furthermore, a purification effect can be obtained by fractionation in the usual manner. In addition, products having a more uniform molecular weight are obtainable as a result.

A component Z1 according to the invention preferably comprises at least one aziridino polymer which has, as its basic framework, a polyether, preferably a polyether based on polytetrahydrofuran (poly-THF) or a propylene glycol/ethylene glycol copolymer or an ethylene glycol/tetrahydrofuran copolymer, irrespective of the manner of preparation.

Further polyaziridino compounds suitable for use in component Z1 are mentioned, for example, in the Offenlegungsschrift DE 15 44 837, p. 3-p. 14.

A composition according to the invention comprises, as component Z2, at least one monofunctional aziridino compound which differs, in its chemical make-up, from at least one compound according to component Z1 in at least one further feature other than the number of the aziridino groups.

As differing features there are suitable, in principle, all features which, besides the number of aziridino groups, allow a clear distinction to be made between at least one compound according to component Z1 and at least one compound according to component Z2. Suitable distinguishing features are, for example, molecular weight or chemical constitution.

There may accordingly be used as monofunctional aziridino compounds, for example, compounds whose average molecular weight is lower or higher than the average molecular weight of the polymers present in component Z1. Likewise, there may be used as monofunctional aziridino compounds, for example, compounds whose chemical make-up differs from at least one polyfunctional compound used in the context of component Z1.

When polymers are used as monofunctional aziridino compounds, those polymers should preferably be of another polymer type than at least one of the polymers used in the context of component Z1.

For example, the monofunctional aziridino compound is provided as a relatively low-molecular-weight aziridino compound having an average molecular weight of less than about 300 or a relatively high-molecular-weight aziridino compound having an average molecular weight of about 300 or of more than about 300.

There are suitable as monofunctional aziridino compounds, for example, compounds as can be obtained by reaction of relatively low-molecular-weight compounds which have a functional group which can react with at least one of the aziridino derivatives already mentioned hereinbefore in the context of the description of the functionalisation of the polymers. For example, aziridino derivatives as can be obtained by reacting relatively low-molecular-weight linear or branched, saturated or unsaturated or cyclic or aromatic alcohols, epoxides or carboxylic acids with aziridino derivatives, for example γ-ethyleneiminopropylamine or 3-ethyleneiminopropan-1-ol, are suitable. Likewise suitable are the compounds provided with appropriate functional groups but monofunctional in terms of aziridino groups as are mentioned in DE 100 26 852 A1 on p. 4, line 20 to p. 7, line 42.

Suitable relatively low-molecular-weight alcohols are, for example, methanol, ethanol, the isomers of propanol, of butanol, of pentanol, of hexanol, of heptanol or of octanol, cycloalkanols having from 6 to about 44 carbon atoms or aromatic alcohols having from 6 to about 22 carbon atoms. The aziridino derivatives of butanol are especially suitable.

Suitable compounds for the preparation of monofunctional aziridino derivatives having a molecular weight of more than about 300, as can be used as a constituent of component Z2 according to the invention, are, for example, monofunctional polymers as have already been described hereinbefore. In that case it is possible, for example, for the same type of polymer to be used as is already present in component Z1. It is, however, likewise possible for a type of polymer to be used which differs from one or more polymer type(s) present in component Z1.

In the context of a preferred embodiment of the present invention, an aziridino compound used as a constituent of component Z2 does not contain an OH, SH, NH or NR group, wherein R denotes a linear or branched, saturated or unsaturated alkyl radical having from 1 up to about 44 carbon atoms.

Especially suitable as monofunctional aziridino compounds having a molecular weight of more than about 300 are polyaddition or polycondensation products having one aziridino group, for example polyester aziridines or polyether aziridines, preferably polyether aziridines.

The preferred polyether aziridines may be, for example, homopolyethers, although copolyethers may also be used. Special preference is given in the context of the present invention to the use of polypropylene glycol which is monofunctional in terms of aziridino functions. Special preference is given to the use of polyethers wherein the end of the chain does not have an OH, SH, NH or NR group as terminal group. For example, polyethers having, at respective termini, one aziridino group and one alkyl group, ester group, amide group or the like are suitable. Especially suitable are polyether compounds which are terminated at one end by means of an ether group having a linear or branched, saturated alkyl group having from 1 to 8 carbon atoms, especially from 2 to 6 carbon atoms.

It has been found that the amount of component Z2 in the composition according to the invention should be so selected in relation to the amount of component Z1 that the ratio of aziridino groups in component Z1 to aziridino groups in component Z2 is from about 20:1 to about 1:1, for example from about 10:1 to about 1.2:1 or from about 5:1 to about 1.5:1.

Preferably, the amount of component Z2 in the composition according to the invention, based on the weight of components Z1 and Z2, is at least about 0.1% by weight and at most about 40% by weight, for example from about 0.2 to about 35 or from about 0.3 to about 30 or from about 0.4 to about 25 or from about 0.5 to about 20% by weight. The afore-mentioned values usually vary according to the molecular weight of component Z2 used.

The consistency of a composition according to the invention is preferably within a range from a disc diameter of about 20 mm to a disc diameter of about 50 mm, especially from a disc diameter of about 25 mm to a disc diameter of about 45 mm, measured in accordance with EN ISO 4823:2000.

In the context of a further embodiment of the present invention, component Z2 of a composition according to the invention differs from component Z1 in one or two or more of the following further features:
i) number average of the molecular weight,
ii) weight average of the molecular weight,
iii) polydispersity,
iv) composition of the polymer backbone,
v) end groups.

In addition to components Z1 and Z2, a composition according to the invention can also comprise an additive or a mixture of two or more additives.

Suitable additives are, for example, compounds that bring about plasticising of the cured dental material compositions. Such compounds can be both typical plasticisers as are also provided for other polymer systems and also esters of polycarboxylic acids, polyaromatic compounds and sulfonic acid esters or compounds which, besides the plasticising, also bring about other effects such as a surfactant action, an increase in structural strength and an improvement in flow behaviour.

Typical plasticisers are, for example, compounds of the ester type such as $C_{12}$- to $C_{15}$-alkyl lactates, ethyl or butyl esters of citric acid or of acetylcitric acid, phthalic acid esters of relatively long, branched alcohols such as bis(2-ethylhexyl)phthalate or phthalic acid polyester, $C_2$- to $C_{22}$-dialkyl esters of $C_2$- to $C_6$-dicarboxylic acids such as bis(2-ethylhexyl) adipate, dioctyl maleate, diisopropyl adipate, aromatic and aliphatic sulfonic acid esters such as $C_2$- to $C_{20}$-alkylsulfonic acid esters of phenol or of $C_1$- to $C_{22}$-alkanols or typical aromatic plasticisers such as polyphenyls in a wide viscosity range, including wax-like polyphenyls such as are obtainable, for example, from the Monsanto company, dibenzyltoluene, isomeric mixtures of $C_{20}$ to $C_{40}$ aromatic compounds, with preference being given to the use of mixtures of plasticisers of the ester type and aromatic type.

An example of a preferred plasticiser mixture is a mixture of acetyl tributyl citrate and dibenzyltoluene.

Likewise suitable as additives are triacyl esters of glycerol of non-animal origin. Suitable additives can consist of, for example, modified fats of vegetable origin such as hydrogenated palm oil or soybean oil or synthetic fats.

Suitable fats are described in DE 197 11 514 A1 (e.g. p. 2, line 65-p. 3, line 22), to the full content of which reference is here made. Avocado oil, cottonseed oil, groundnut oil, cocoa butter, pumpkin seed oil, linseed oil, maize germ oil, olive oil, palm oil, rice oil, rapeseed oils, safflower oil, sesame oil, soybean oil, sunflower oil, grapeseed oil, wheat germ oil, Borneo tallow, fulwa butter, hemp oil, illlipé butter, lupin oils, candlenut oil, kapok oil, katiau fat, kenaf seed oil, kekuna oil, poppy seed oil, mowrah butter, okra oil, perilla oil, sal butter, shea butter and tung oil are especially suitable, provided that the fats in question have been hydrogenated before use. Suitable hydrogenated fats are considered to be those whose iodine value is less than 20 (measured in accordance with the DGF [German Society for Fat Science] standard C-V 11 Z2). Fat hydrogenation procedures are described, for example, in "Ullmanns Enzyklopädie der industriellen Chemie", 4th edition, volume 11, p. 469.

Mixtures of those naturally occurring fats, and also synthetically prepared fats such as Softisan 154 or Dynasan 118 (from Hüls) can likewise be used. The preparation of such synthetic triacyl glycerides is relatively simple for the person skilled in the art and can be carried out by starting from glycerol and the appropriate fatty acid methyl esters. Such esterification reactions are described in, inter alia, "Houben-Weyl, Methoden der Organischen Chemie", Vol. E5/Part 1, p. 659 ff.

Preferred triacyl glycerides correspond to the formula:

in which $R^1$, $R^2$ and $R^3$ denote, each independently of the others, $C_{11}H_{23}CO$, $C_{13}H_{27}CO$, $C_{15}H_{31}CO$ or $C_{17}H_{35}CO$. Mixtures of such triacyl glycerides also come into consideration.

Likewise suitable as additives are liquid polymeric compounds having molecular weights of more than about 2000 g/mol, for example types of compounds such as polyethers, polyesters, polyurethanes, polycarbonates or polyolefins, with hydroxyl, ether, alkyl and acyl groups being suitable as end groups.

A special compound class of liquid polymers is represented by those of the polyether type.

In that case, those polyethers which have a molecular weight the same as or similar to the aziridino polyethers used in component Z1 are especially outstanding.

For example, dihydroxy or diacetyl polyethers comprising oxytetramethylene and oxydimethylene units in a ratio of from 4:1 to 3:1 and molecular weights in the range from 3000 to 8000 g/mol are suitable as additives.

Polypropylene oxide polyols and/or copolymerisation products and/or block copolymerisation products of ethylene oxide and propylene oxide having hydroxyl or acetyl end groups can also be used in admixture with the mentioned polyethers or on their own as additives.

In the case of block copolymerisation products having molecular weights greater than 2000 g/mol, the solubility-promoting action of those surfactant-like compounds can be additionally utilised.

Furthermore, as a result of selecting and mixing the aforementioned polyether derivatives, the flow behaviour and the requisite adjustment of hydrophilicity and hydrophobicity of the mixed preparations can be decisively influenced.

The compositions according to the invention may also comprise, as additives, from 10 to 15% by weight fillers having reinforcing action.

For that purpose there may be used organic and inorganic solids which, in the compositions according to the invention, do not give rise to any undesirable reactions during storage and which, after mixture of separately stored components, do not adversely affect the course of setting. For example, silicic acid, zinc oxide, calcium carbonate, barium sulphate, quartz powder, heavy spar, fluorspar, calcium phosphate or kaolin are suitable for that purpose.

In that context, fillers having an $SiO_2$ content of more than about 50% by weight, for example at least about 90% by weight, such as quartz powder and fine-particle silicic acids of synthetic or natural origin, have been found to be especially advantageous.

For example, pyrogenic silicic acids and precipitated silicic acids, which are usually used in surface-modified form, and also diatomaceous earth from various sources are suitable.

Mixtures of processed diatomaceous earth that has a pH, in a 5% aqueous suspension, of from 8 to 10 and pyrogenic surface-modified silicic acid having BET surface areas of from 100 to 600 $m^2/g$ are especially suitable.

The preparations according to the invention may also comprise further additives such as dyes and coloured pigments, disinfectants, aromas or flavourings.

Acid capture agents, which fully neutralise acids, acid groups or acid-cleaving substances present in the starting materials, may also be used as additives. For example, amines, especially tertiary amines, are suitable for the purpose.

As additives there may also be used modifying agents as are described in DE 32 45 052 (p. 4-p. 6), with reference being made expressly to the modifying agents mentioned therein, which are understood as being part of the disclosure of the present text.

The above-mentioned additives are usually contained in a composition according to the invention in an amount of from 0 to about 60% by weight, for example from about 10 to about 40% by weight.

The compositions according to the invention can, in principle, be obtained in any manner known to the person skilled in the art. For example, the individual constituents of the composition are mixed together in one or more consecutive steps using suitable mixing apparatus. The present invention accordingly relates also to a process for the preparation of a composition according to the invention, wherein two components Z1 and Z2 are mixed together, there being used,
 a) as component Z1, at least one polyaddition product or at least one polycondensation product having on average 2 aziridino groups or more and a molecular weight of at least 1000 and
 b) as component Z2, at least one compound having 1 aziridino group, and
at least one compound according to component Z2 differing, in its chemical make-up, from at least one compound according to component Z1 in at least one further feature other than the number of the aziridino groups.

A composition according to the invention is suitable for producing dental materials.

The present invention accordingly relates also to a dental material comprising at least one basic component B and at least one catalyst component K, component B comprising at least one composition according to the invention and component K comprising at least one catalyst for the cross-linking of at least part of component B.

For production of a dental material according to the invention, a composition according to the invention, as basic component B, is mixed together with a catalyst component K.

The catalyst component K comprises at least one initiator substance which triggers polymerisation of the aziridino-group-carrying constituents of component B and, as a result, curing of the dental material as a whole.

As initiator substances there come into consideration, in principle, all compounds triggering the polymerisation of aziridines, provided that they bring about a suitable setting rate and suitable elastomeric properties for the cured dental material.

Accordingly, for use in two-component impression materials based on the polyether derivatives described hereinbefore there are suitable those initiator substances which make possible curing of the mixed preparation at room temperature in a period of from 1 to 20 minutes to form a resilient solid body, that solid body meeting the requirements for a resilient impression material according to DIN/EN 2482 and having a Shore A hardness (DIN 53 505) of at least 20 after 24 hours.

In the context of a preferred embodiment of the present invention, a dental material according to the invention is so adjusted with respect to components B and K that it has after mixing of the basic component B and the catalyst component K at room temperature, within a period of 20 minutes or less, a Shore A hardness of at least 80% of the value of Shore A hardness reached after 24 hours.

As initiator substances in a catalyst component K which is suitable according to the invention there may be used, in principle, all known initiators. There are advantageously used those initiators or initiator systems which permit simple adjustment of the course of curing, which do not bring about subsidiary effects and which make it possible to achieve, reproducibly, the requisite level of mechanical properties.

A summarising description of the initiator substances used for the curing of N-alkylaziridino compounds is contained in, for example, O. C. DERMER, G. E. HAM, "Ethylenimine and other Aziridines" Academic Press (1969).

Trialkylsulfonium salts as are described in, for example, U.S. Pat. No. 4,167,618 (e.g.: column 2, line 36-column 4, line 32 and Examples) are especially suitable as initiator substances. The mentioned trialkylsulfonium salts are understood as being part of the disclosure of the present text.

In the patent specification DE 914 325, the use of oxonium, ammonium and sulfonium salts as initiator substances is proposed (e.g.: p. 2, line 77-p. 3, line 100 and Examples), the initiator substances mentioned therein likewise being considered part of the disclosure of the present text.

In the patent application DE 100 18 918 A1, initiators are described which impart just a low degree of acidity to the catalyst component and which make possible a readily adjusted, relatively long processing time after mixing of the basic component and catalyst component has been carried out. Reference is expressly made also to the compounds mentioned therein and the initiator substances mentioned therein are likewise considered part of the disclosure of the present text.

The initiator compounds mentioned in U.S. Pat. No. 4,167,618 are especially suitable. The disclosure of that publication in respect of initiator substances is considered part of the disclosure of the present text.

Initiator systems of that type are suitable for curing the basic components according to the invention at the requisite rate. By virtue of their use, the desired properties of the resilient solid body can be achieved.

The patent application DE-199 42 459 describes elastomeric materials having an improved catalyst component which are distinguished by increased extensibility. In accordance with that invention, boric acid complexes are used as initiators. Those initiators have likewise been found to be suitable for the curing of N-alkylaziridino polymers in accordance with the present invention and can be used in the context of the present invention.

In the context of the present invention, the following initiator compounds are preferably used: the zinc salt of p-toluenesulfonic acid, β-(S-lauryl-S-ethylsulfonium)butyronitrile tetrafluoroborate, dodecylbenzenesulfonic acid zinc salt, β-(S-lauryl-S-ethylsulfonium)-β-phenylacrylic acid butyl ester tetrafluoroborate.

A catalyst component K used in accordance with the invention may also comprise, in addition to one of the above-mentioned initiator compounds or a mixture of two or more thereof, one or more additives. The additives already mentioned hereinbefore in the context of the present text are suitable as additives.

The initiator compounds of component K may be, for example, in the form of low-viscosity liquids or solids which may be difficult to incorporate uniformly in the more or less viscous masses of component B. In order to avoid that disadvantage, the initiator compounds may be brought into a viscous form corresponding to the particular intended application area, for example by incorporating fillers of large surface area, such as colloidal silica.

Also, the use of solutions of the initiator compounds in suitable plasticisers as component K is often advantageous; by that means not only is it possible for extreme mixing ratios to be avoided but it is also possible for cross-linking agents that are solid at room temperature, e.g. acetyl tributyl citrate, to be conveniently incorporated into component K.

For example, a component K that is suitable according to the invention comprises at least one of the following classes of compounds, which bring about plasticising of the cured dental materials, namely A typical plasticisers having molecular weights of less than 500 g/mol, B triacyl glycerides that are solid at room temperature, having molecular weights in the range from 500 to 2000 g/mol, or C polymers that are liquid at room temperature, having molecular weights of more than 2000 g/mol, or a mixture of two or more thereof.

The initiator compounds are generally contained in component K in an amount of from 0.5 to 90% by weight, for example from 2 to 80% by weight or from about 5 to about 50% by weight.

In order to produce the dental materials according to the invention, components B and K are mixed together in suitable quantitative ratios.

The mixing is advantageously carried out in practice by means of continuous mixers, usually consisting of a storage container containing components B and K and static or dynamic mixing elements.

Using such apparatus it is possible to achieve sufficient quality of mixing, which can easily be checked by means of the uniform coloration.

Usually, in the case of polyether-based dental materials, the volumetric mixing ratio or the weight ratio between catalyst component K and basic component B is adjusted to values of from about 3:1 to about 1:10, with special preference being given to adjustments of from about 1:2 to about 1:5, especially about 1:2 or about 1:5.

The molar ratio of aziridino groups to anions of the initiator compounds is, in the context of the dental materials according to the invention, from about 3:1 to about 0.9:1, for example from about 2:1 to about 1:1, especially from about 1.8:1 to about 1.2:1.

From the values mentioned it can accordingly be seen that the composition of components K and B can, in dependence on the desired molar ratio of the reactive aziridino groups to the anions of the initiator compound or of the mixture of two or more initiator compounds, vary within wide ranges.

The polyether-based dental materials according to the invention, having improved release properties and improved flow-in properties, are obtained, for example, from preparations containing, in total, about 30 to 80% by weight, preferably 45 to 71% by weight, aziridino-group-carrying compounds;

8 to 40% by weight, preferably 10 to 25% by weight, compounds which bring about plasticising of the cured dental materials;

4 to 25% by weight, preferably 9 to 16% by weight, fillers;

4 to 20% by weight, preferably 4 to 16% by weight, further active ingredients such as colorants, aromas, initiators, retarding agents, accelerators, rheological additives, consistency agents and surfactants.

Especially suitable components and formulations are described, for example, in the following patents and patent applications: DE 1745810, U.S. Pat. Nos. 3,453,242, 1,544, 837, 4,167,618, DE 3245052, DE 3728216, EP 0421371, DE 4306997, DE 4321257, DE 19753461, DE 19740234, DE 10001747, DE 10018918.

The preparations according to the invention can be used in very different dental materials employed in dental medicine or dental technology. Preferred areas of use of such dental materials are single-phase and two-phase impression-taking in dental medicine and bite registration.

The invention relates also to containers and mixing devices containing materials produced from the preparations according to the invention, especially dental materials, for example cartridges, sachets, impression trays, static and dynamic mixers and mixing devices.

The invention relates also to a kit for producing dental materials, comprising at least one composition according to the invention as component B and at least one component K comprising a catalyst for the cross-linking of at least part of component B, wherein components B and K are present separated from one another.

Furthermore, the present invention relates to the use of a composition according to the invention as basic component B for coatings, impression materials, seals or dental moulding materials.

Furthermore, the present invention relates also to the use of a compound having one aziridino group in accelerating the setting rate of dental materials according to the invention.

The invention is explained in greater detail hereinbelow by means of working examples.

WORKING EXAMPLES

Measurements

Measurement of the Shore A hardness is a method known to the person skilled in the art for measuring the degree of curing. Time-dependent measurements were carried out according to DIN 53505.

The rheological tests were carried out using a rotary viscometer of the type CVO 120 HR from the company Bohlin Instruments GmbH Pforzheim. The measurements were carried out at 23° C. A plate-plate geometry was used; the plate diameter was 20 mm. The dynamic viscosity $\eta$ was determined as a function of the shear rate $\dot{\gamma}$.

The tear strength and elongation values given hereinbelow were determined by analogy with DIN 50125, Form B. A Zwick 1435 universal testing machine from the company Zwick GmbH & Co Ulm was used as test apparatus. The test mould for producing the test specimens consists of 2 half-moulds made from brass in accordance with DIN 50125, Form B and has a diameter of 6.0±0.1 mm and a measured length of 50.0±0.1 mm (tensile test B 6×50 DIN 50125).

For sample preparation, the basic and catalyst components are mixed in the defined volumetric ratio of 5:1±1 ml until homogeneous and introduced into the half-mould. The half-mould is put together and the test specimen is removed after 10 minutes at 23° C. The test specimens are then stored at 23° C. and 50% relative humidity for 24±4 hours and then measured. The values given were determined by means of 5 parallel measurements.

Formulations

The basic component used in the context of the following Examples had the following composition, the content of plasticiser having been replaced by the amount of monofunctional monomers given in each case in the following Tables:

55.5% difunctional monomer (copolymer of ethylene oxide and THF having a molecular weight of 6000)
14.2% fat (triacyl esters of glycerol of non-animal origin)
18.1% plasticiser (dibenzyltoluene)
12.2% filler (diatomaceous earth).

1. Test with varying proportions of monofunctional monomers

Catalyst component: zinc salt of p-toluenesulfonic acid
Basic component B: plasticiser replaced by monofunctional monomer
Monofunctional monomer used: tert-butanol functionalised with ethyleneimine

TABLE 1

| Monomers used | | | Shore A hardness after | | | |
|---|---|---|---|---|---|---|
| Mono-functional monomer | Di-functional monomer | Ethyleneimine groups in 100 g of basic component | 10 min | 15 min | 30 min | 24 h |
| 1.55% | 55.0% | 2.50 10$^{-2}$ mol | 37 | 43 | 49 | 54 |
| 1.16% | 55.0% | 2.32 10$^{-2}$ mol | 36 | 43 | 49 | 54 |
| 0.78% | 55.0% | 2.14 10$^{-2}$ mol | 35 | 42 | 48 | 54 |
| 0.39% | 55.0% | 1.96 10$^{-2}$ mol | 33 | 41 | 48 | 54 |
| 0% | 55.0% | 1.77 10$^{-2}$ mol | 31 | 40 | 48 | 54 |

Monofunctional monomer used: polypropylene glycol monobutyl ether functionalised with ethyleneimine, M=1000 (before functionalisation):

TABLE 2

| Monomers used | | | Shore A hardness after | | | |
|---|---|---|---|---|---|---|
| Mono-functional monomer | Di-functional monomer | Ethyleneimine groups in 100 g of basic component | 10 min | 15 min | 30 min | 24 h |
| 10.0% | 55.0% | 2.50 10$^{-2}$ mol | 35 | 42 | 48 | 55 |
| 7.5% | 55.0% | 2.32 10$^{-2}$ mol | 34 | 42 | 48 | 55 |
| 5.0% | 55.0% | 2.14 10$^{-2}$ mol | 34 | 42 | 49 | 55 |
| 2.5% | 55.0% | 1.96 10$^{-2}$ mol | 32 | 41 | 48 | 54 |
| 0% | 55.0% | 1.77 10$^{-2}$ mol | 31 | 41 | 48 | 54 |

TABLE 3

| Monomers used | | Viscosity | | Tensile strength | Extensibility before rupture |
|---|---|---|---|---|---|
| Mono-functional monomer | Di-functional monomer | $\dot{\gamma} = 20$ 1/s | $\dot{\gamma} = 50$ 1/s | | |
| 0.0% | 55.0% | 165 Pas | 105 Pas | 1.21 ± 0.08 MPa | 95% |
| 10.0% | 55.0% | 120 Pas | 85 Pas | 1.32 ± 0.08 MPa | 92% |
| 17.6% | 55.0% | 135 Pas | 95 Pas | 1.38 ± 0.03 MPa | 99% |

2. Test with varying proportions of monofunctional monomers and adjustment of the content of polymerisation initiator (molar ratio of ethyleneimine:anion of the polymerisation initiator=1.4:1.0)

a) Catalyst component: zinc salt of p-toluenesulfonic acid
Basic component: plasticiser replaced by monofunctional monomer
Monofunctional monomer used: polypropylene glycol monobutyl ether functionalised with ethyleneimine, M=1000 (before functionalisation):

TABLE 4

| Monomers used | | Shore A hardness after | | | | | |
|---|---|---|---|---|---|---|---|
| Mono-functional monomer | Di-functional monomer | 6 min | 8 min | 10 min | 15 min | 30 min | 24 h |
| 10.0% | 55.0% | 29 | 40 | 45 | 52 | 56 | 58 |
| 7.5% | 55.0% | 25 | 36 | 42 | 49 | 55 | 57 |
| 5.0% | 55.0% | 20 | 34 | 39 | 47 | 53 | 56 |
| 2.5% | 55.0% | 16 | 28 | 35 | 44 | 51 | 56 |
| 0% | 55.0% | 11 | 19 | 28 | 38 | 47 | 55 | b) Catalyst component: dodecylbenzenesulfonic acid salt
Basic component: plasticiser replaced by monofunctional monomer
Monofunctional monomer used: polypropylene glycol monobutyl ether functionalised with ethyleneimine, M=1000 (before functionalisation):

TABLE 5

| Monomers used | | Shore A hardness after | | | | | |
|---|---|---|---|---|---|---|---|
| Mono-functional monomer | Di-functional monomer | 6 min | 8 min | 10 min | 15 min | 30 min | 24 h |
| 10.0% | 55.0% | 40 | 48 | 51 | 56 | 57 | 58 |
| 7.5% | 55.0% | 40 | 47 | 51 | 54 | 55 | 57 |
| 5.0% | 55.0% | 39 | 45 | 49 | 53 | 54 | 57 |
| 2.5% | 55.0% | 37 | 44 | 48 | 53 | 54 | 57 |
| 0% | 55.0% | 31 | 42 | 46 | 51 | 54 | 56 | c) Catalyst component: p-toluenesulfonic acid
Basic component: plasticiser replaced by monofunctional monomer
Monofunctional monomer used: polypropylene glycol monobutyl ether functionalised with ethyleneimine, M=1000 (before functionalisation):

TABLE 6

| Monomers used | | Shore A hardness after | | | | | |
|---|---|---|---|---|---|---|---|
| Mono-functional monomer | Di-functional monomer | 6 min | 8 min | 10 min | 15 min | 30 min | 24 h |
| 10.0% | 55.0% | 18 | 25 | 30 | 39 | 44 | 50 |
| 7.5% | 55.0% | 19 | 26 | 32 | 38 | 43 | 49 |
| 5.0% | 55.0% | 17 | 25 | 30 | 38 | 43 | 49 |
| 2.5% | 55.0% | 19 | 26 | 32 | 39 | 45 | 50 |
| 0% | 55.0% | 12 | 20 | 26 | 33 | 41 | 48 | d) Catalyst component: tetrafluoroborate sulfonium salt
Basic component: plasticiser replaced by monofunctional monomer
Monofunctional monomer used: polypropylene glycol monobutyl ether functionalised with ethyleneimine, M=1000 (before functionalisation):

| Monomers used | | Shore A hardness after | | | | | |
|---|---|---|---|---|---|---|---|
| Mono-functional monomer | Di-functional monomer | 6 min | 8 min | 10 min | 15 min | 30 min | 24 h |
| 10.0% | 55.0% | 37 | 44 | 46 | 49 | 50 | 50 |
| 7.5% | 55.0% | 35 | 41 | 45 | 48 | 49 | 49 |
| 5.0% | 55.0% | 34 | 40 | 44 | 47 | 48 | 49 |
| 2.5% | 55.0% | 32 | 38 | 43 | 46 | 48 | 49 |
| 0% | 55.0% | 32 | 39 | 41 | 45 | 47 | 47 |

The invention claimed is:

1. A composition comprising:
at least one catalyst component K comprising an initiator selected from the group consisting of an oxonium salt, an ammonium salt, a sulfonium salt, p-toluenesulfonic acid, zinc salt of p-toluenesulfonic acid, dodecylbenzenesulfonic acid salt, and combinations thereof; and
at least one basic component B comprising at least the two components Z1 and Z2,
wherein component Z1 comprises at least one polyaddition product or at least one polycondensation product having on average 2 aziridino groups or more and a molecular weight of at least 1000, with the proviso that component Z1 does not comprise polydimethylsiloxanes, and
wherein component Z2comprises at least one compound having only 1 aziridino group, at least one compound according to component Z2 differing, in its chemical make-up, from at least one compound according to component Z1 in at least one further feature other than the number of the aziridino groups, the difference from component Z1 comprising at least one or two or more of the following further features:
i) number average of the molecular weight,
ii) weight average of the molecular weight,
iii) polydispersity,
iv) composition of the polymer backbone, and
v) end groups, and
wherein the amount of component Z2 in the composition is about 0.4% by weight to about 25% by weight, based on the total weight of components Z1 and Z2.

2. A composition according to claim 1, wherein component Z1 comprises at least one polymer selected from the group consisting of polyethers, polyesters, and polyurethanes.

3. A composition according to claim 1, wherein component Z1 comprises a polyether having at least a proportion of tetrahydrofuran units.

4. A composition according to claim 1, wherein component Z2 comprises a compound selected from the group consisting of polyethers, polyesters, polyurethanes, and polydimethylsiloxanes.

5. A composition according to claim 1, wherein component Z2 comprises a compound having a molecular weight of 300 or more.

6. A composition according to claim 1, further comprising an additive or a mixture of two or more additives.

7. A process for the preparation of a composition, comprising:
providing a catalyst component K comprising an initiator selected from the selected from the group consisting of an oxonium salt, an ammonium salt, a sulfonium salt, p-toluenesulfonic acid, zinc salt of p-toluenesulfonic acid, dodecylbenzenesulfonic acid salt, and combinations thereof; and
preparing basic component B by a process comprising mixing two components Z1 and Z2 together,
wherein component Z1 comprises at least one polyaddition product or at least one polycondensation product having on average 2 aziridino groups or more and a molecular weight of at least 1000, with the proviso that component Z1 does not comprise polydimethylsiloxanes, and
wherein component Z2 comprises at least one compound having only 1 aziridino group, and at least one compound according to component Z2 differing, in its chemical make-up, from at least one compound according to component Z1 in at least one further feature other than the number of the aziridino groups, the difference from component Z1 comprising at least one or two or more of the following further features:
i) number average of the molecular weight,
ii) weight average of the molecular weight,
iii) polydispersity,
iv) composition of the polymer backbone, and
v) end groups, and
wherein mixing two components Z1 and Z2 together comprises mixing an amount of component Z2 that is about 0.4% by weight to about 25% by weight, based on the total weight of components Z1 and Z2.

8. A dental material comprising at least one composition according to claim 1.

9. A dental material according to claim 8, wherein after mixing of basic component B and catalyst component K at room temperature, the dental material has within a period of 20 minutes or less, a Shore A hardness of at least 80% of the value of Shore A hardness reached after 24 hours.

10. A method of using a dental material according to claim 8 comprising forming coatings, impression materials, seals, or dental moulding materials.

11. A method of accelerating the setting rate of a dental material according to claim 8, comprising using a compound having only 1 aziridino group.

12. A kit for producing dental materials, comprising a composition according to claim 1, wherein the components B and K are present separated from one another.

13. A container or mixing device comprising a dental material according to claim 8.

14. A composition comprising:
at least one catalyst component K comprising an initiator selected from the selected from the group consisting of an oxonium salt, an ammonium salt, a sulfonium salt, p-toluenesulfonic acid, zinc salt of p-toluenesulfonic acid, dodecylbenzenesulfonic acid salt, and combinations thereof; and
at least one basic component B comprising at least the two components Z1 and Z2,
wherein component Z1 comprises at least one polyaddition product or at least one polycondensation product selected from the group consisting of polyethers, polyesters, and polyurethanes, and having on average two aziridino groups or more and a molecular weight of at least 1000, and
wherein component Z2 comprises at least one compound having only one aziridino group, and wherein the at least one compound having only one aziridino group differs, in its chemical make-up, from at least one compound according to component Z1 in at least one further feature other than the number of the aziridino groups, the difference from component Z1 comprising at least one or two or more of the following further features:
i) number average of the molecular weight,
ii) weight average of the molecular weight, iii) polydispersity,
iv) composition of the polymer backbone, and
v) end groups, and
wherein the amount of component Z2 in the composition is about 0.4% by weight to about 25% by weight, based on the total weight of components Z1 and Z2.

15. A process for the preparation of a composition, comprising:
providing a catalyst component K comprising an initiator selected from the selected from the group consisting of an oxonium salt, an ammonium salt, a sulfonium salt, p-toluenesulfonic acid, zinc salt of p-toluenesulfonic acid, dodecylbenzenesulfonic acid salt, and combinations thereof; and
preparing basic component B by a process comprising mixing two components Z1 and Z2 together,
wherein component Z1 comprises at least one polyaddition product or at least one polycondensation product selected from the group consisting of polyethers, polyesters, and polyurethanes, and having on average two aziridino groups or more and a molecular weight of at least 1000, and wherein component Z2 comprises at least one compound having only one aziridino group, and wherein the at least one compound having only one aziridino group differs, in its chemical make-up, from at least one compound according to component Z1 in at least one further feature other than the number of the aziridino groups, the difference from component Z1 comprising at least one or two or more of the following further features:
i) number average of the molecular weight,
ii) weight average of the molecular weight,
iii) polydispersity,
iv) composition of the polymer backbone, and
v) end groups, and
wherein mixing two components Z1 and Z2 together comprises mixing an amount of component Z2 that is about 0.4% by weight to about 25% by weight, based on the total weight of components Z1 and Z2.

* * * * *

UNITED STATES PATENT AND TRADEMARK OFFICE
CERTIFICATE OF CORRECTION

PATENT NO.         : 7,923,485 B2
APPLICATION NO.    : 10/524301
DATED              : April 12, 2011
INVENTOR(S)        : Thomas Klettke It is certified that error appears in the above-identified patent and that said Letters Patent is hereby corrected as shown below:

Title Page, item (56);
On Page 2 Other Publications
Column 1
Line 1, Delete "Zhahnheilkunde" and insert -- Zahnheilkunde --, therefor.
Line 4, Delete "12," and insert -- 15, --, therefor.

Column 17
Line 29, In Claim 1, delete "Z2comprises" and insert -- Z2 comprises --, therefor.
Line 63, In Claim 7, after "initiator" delete "selected from the".

Column 18
Line 45, In Claim 14, after "initiator" delete "selected from the".

Column 19
Line 10, In Claim 15, after "initiator" delete "selected from the".

Signed and Sealed this
Thirteenth Day of September, 2011

David J. Kappos
*Director of the United States Patent and Trademark Office*